(12) United States Patent
Lesieur

(10) Patent No.: US 7,752,895 B2
(45) Date of Patent: Jul. 13, 2010

(54) METHOD FOR USING AN ALTERNATE PRESSURE VISCOMETER

(75) Inventor: Yves Lesieur, Le Havre (FR)

(73) Assignee: Chevron Oronite S.A., Cedex (FR)

( * ) Notice: Subject to any disclaimer, the term of this patent is extended or adjusted under 35 U.S.C. 154(b) by 135 days.

(21) Appl. No.: 11/904,838

(22) Filed: Sep. 28, 2007

(65) Prior Publication Data

US 2008/0127718 A1 Jun. 5, 2008

Related U.S. Application Data

(60) Provisional application No. 60/868,038, filed on Nov. 30, 2006.

(51) Int. Cl.
*G01N 11/08* (2006.01)
(52) U.S. Cl. ..................................................... 73/54.09
(58) Field of Classification Search ............... 73/54.06, 73/54.09
See application file for complete search history.

(56) References Cited

U.S. PATENT DOCUMENTS

| | | | |
|---|---|---|---|
| 3,137,161 A | 6/1964 | Lewis et al. | |
| 3,277,694 A | 10/1966 | Cannon et al. | |
| 3,604,247 A | 9/1971 | Gramain et al. | |
| 3,725,010 A | 4/1973 | Penhast | |
| 3,808,877 A | 5/1974 | Blair | |
| 3,895,513 A | 7/1975 | Richardson | |
| 4,517,830 A | 5/1985 | Gunn et al. | |
| 4,723,442 A | 2/1988 | Manning et al. | |
| 4,858,127 A | 8/1989 | Kron et al. | |
| 4,890,482 A * | 1/1990 | Maini ........................ | 73/54.14 |
| 5,142,899 A | 9/1992 | Park et al. | |
| 5,172,585 A | 12/1992 | Gleissle | |
| 5,257,529 A | 11/1993 | Taniguchi et al. | |
| 5,272,912 A * | 12/1993 | Katsuzaki ................... | 73/54.08 |
| 5,756,883 A | 5/1998 | Forbes | |
| 5,847,268 A | 12/1998 | Ball | |
| 5,877,409 A | 3/1999 | Girling | |
| 6,393,898 B1 | 5/2002 | Hajduk et al. | |
| 6,412,337 B1 | 7/2002 | Arzate et al. | |
| 6,571,608 B2 | 6/2003 | Shin et al. | |
| 6,575,019 B1 | 6/2003 | Larson | |
| 6,584,830 B2 | 7/2003 | Long | |
| 6,732,574 B2 | 5/2004 | Hajduk et al. | |
| 6,907,772 B2 | 6/2005 | Kensey et al. | |
| 6,915,679 B2 | 7/2005 | Chien et al. | |
| 6,990,850 B2 | 1/2006 | Taylor | |
| 2002/0148282 A1* | 10/2002 | Hajduk et al. .............. | 73/54.07 |

(Continued)

FOREIGN PATENT DOCUMENTS

DE 3331659 A1 4/1985

(Continued)

*Primary Examiner*—Hezron Williams
*Assistant Examiner*—Nathaniel Kolb
(74) *Attorney, Agent, or Firm*—Joseph P. Foley; Claude J. Caroli

(57) ABSTRACT

A method for determining the viscosity and relative change of viscosity of a fluid over plural shear rates caused by a decreasing or increasing pressure differential resulting from fluid flow to a defined chamber in a capillary system. The flow of liquid through the capillary restriction, the pressure variation rate and known dimensions of the system can be used typically by a processor to determine a rheological property of a fluid.

10 Claims, 10 Drawing Sheets

U.S. PATENT DOCUMENTS

| | | |
|---|---|---|
| 2003/0158500 A1 | 8/2003 | Kensey et al. |
| 2004/0211247 A1 | 10/2004 | Hajduk et al. |
| 2006/0065044 A1 | 3/2006 | Tsang et al. |
| 2006/0179923 A1 | 8/2006 | Burns et al. |

FOREIGN PATENT DOCUMENTS

| | | |
|---|---|---|
| DE | 19934840 A1 | 2/2001 |
| EP | 0492664 A1 | 7/1992 |
| EP | 1 134 575 A1 | 9/2001 |
| GB | 924688 A | 5/1963 |
| GB | 1184089 A | 3/1970 |
| GB | 1337322 A | 11/1973 |
| GB | 1399783 A | 7/1975 |
| WO | WO 2004/063722 A1 | 7/2004 |
| WO | WO 2006/066565 A1 | 6/2006 |

* cited by examiner

FIG.7 Example of oxidation curve

Example of Nitro oxidation curves

Effect of oxidation on a VII

METHOD FOR USING AN ALTERNATE PRESSURE VISCOMETER

FIELD OF THE INVENTION

The present invention is directed to a method for determining the viscosity and relative change of viscosity of a fluid over plural shear rates caused by a decreasing or increasing pressure differential resulting from fluid flow to a defined chamber in a capillary system using an alternate pressure viscometer device. The flow of liquid through the capillary restriction, the pressure variation rate and known dimensions of the system can be related, typically by a processor, for determining a rheological property of a fluid. More particularly, the process can monitor the relative increase of apparent viscosity with regard to oxidative thickening.

BACKGROUND OF THE INVENTION

Rheology is branch of physics dealing with the deformation and flow of matter. It is particularly concerned with the properties of matter that determine its behavior when a force is exerted on it. Thus, it is concerned with the study of the change in form and flow of matter, embracing viscosity, elasticity and plasticity. The present application is directed to the subset of fluid dynamics concerned with the flow of fluids, primarily liquids in Newtonian and non-Newtonian regimes. Rheological relationships can provide a direct assessment of processability, are useful for monitoring and controlling a process, are a sensitive method for material characterization (such as changes to the molecular weight), and useful for following the course of a chemical reaction or changes to a fluid in simulated conditions. Rheological measurements allow the study of chemical, mechanical, thermal effects, effects of additives, or the course of reaction byproducts. All measurements of viscosity involve imparting motion to a fluid and observing the resulting deformation of that fluid.

Viscosity is a physical property that characterizes the flow resistance of a fluid. It has been defined as a measure of the internal friction of a fluid where the friction becomes apparent when a layer of fluid is made to move in relation to another layer. It is the resistance experienced by one portion of a material moving over another portion of the material. Viscosity is commonly used to characterize petroleum fluids, such as fuels and lubricants, and often they are specified in the trading and classification of petroleum products. Kinematic viscosity for petroleum products is commonly measured in a capillary viscometer by a standard method such as the ASTM D445 standard. The ASTM D445 standard involves measuring the time for a fixed amount of liquid to flow under gravity through a calibrated glass capillary under a reproducible driving head and a closely controlled temperature. In practice, this method has some challenges due to size limits of the apparatus, due to geometry, the relative sample size, and difficulty in changing shear rates. In addition, the calibrated glass tubes are fragile, difficult to clean, and relatively expensive. Therefore, it is undesirable to use a capillary viscometer for samples which would tend to diminish the repeatability of the capillary tube for example by coating the tubes, since these tubes would need to be removed and cleaned or disposed of prior to reuse. Changing glass capillary tubes in the ASTM D445 standard is a cumbersome and delicate procedure with a process delay since the replacement glass capillary and temperature bath must come to equilibrium.

Viscometers commonly are separated into three main types: Capillary, rotational and moving body. Most of these viscometers can produce viscosity measurements at a specified constant shear rate. Therefore, in order to measure the viscosity over a range of shear rates, one needs to repeat the measurement by changing the parameters (such as height, capillary tube dimensions) for capillary tube viscometers, by changing the rotating speed of the cone or cup in rotating viscometers, or changing the density of the falling object in the moving body viscometer.

The capillary tube viscometer has been principally defined by the Hagen-Poiseuille Equation especially for Newtonain fluids. In a Newtonian fluid the shear stress is proportional to the shear rate, and the proportionality constant is called the viscosity. To measure viscosity with a capillary tube viscometer, the pressure drop and flow rate are independently measured and correlated to some standard fluid of known viscosity. The three general types of glass capillary viscometers most frequently used include the modified Ostwald types for transparent liquids (Cannon-Fenske routine), the suspended level type for transparent liquids (Cannon-Ubbelohde types) and the transverse-flow for transparent and opaque liquids (British Standard BS U-tube reverse flow). While there are precise instructions for operating each of the above capillary viscometers, generally all follow the same set of basic steps. The test sample is inserted into the viscometer and temperature controlled. After reaching test temperature the test sample is allowed to flow under gravity past two timing marks with time recorded on the calibrated capillary tube. Thus, the driving force is the hydrostatic head of the test liquid. The viscosity is calculated as a product of the flow time and the calibration constant. External pressure can be applied to many of the capillary viscometers to increase the range of measurement to enable the study of non-Newtonian behavior.

SUMMARY OF THE INVENTION

The present invention is directed in part to a method for determining the rheological property of a fluid, such as viscosity and relative change of viscosity of a fluid, over a plurality of shear rates caused by a decreasing or increasing pressure differential resulting from fluid flow to a defined chamber in a capillary system using an alternate pressure viscometer device. The flow of liquid through the capillary restriction, the pressure variation rate and known dimensions of the system can be related, typically by a processor, for determining a rheological property of a fluid. More particularly, the process can monitor the relative increase of apparent viscosity with regard to oxidative thickening. Accordingly, disclosed is a method for screening or determining a rheological property of fluid comprising:

a) providing a fluid sample to a reservoir placed in a thermostatic control system;

b) placing a capillary in fluid communication with the fluid sample, wherein the capillary has a first end and a second end with a substantially uniform diameter over a predetermined length, the first end being submerged in the fluid sample to be measured, the second end attached to a manifold having at least one selectable valve, the capillary together with the manifold and the at least one selectable valve define a chamber of predetermined volume;

c) actuating at least one selectable valve attached to the manifold to allow a gas to enter into and pass through the manifold and capillary;

d) inducing the sample into the capillary by rapidly generating a dynamic differential pressure in the chamber thus allowing the sample to flow from the reservoir through the capillary;

e) detecting pressure change of the chamber as a result of the fluid flow; and f) relating the rate of pressure change to a rheological property.

Rheological measurements allow for the study of chemical, mechanical, and thermal treatments, the effects of additives, the course of a reaction, and can be used to predict and control numerous product properties, performance aspects and material behavior. A particularly preferred rheological property is viscosity and/or variation of viscosity. The viscosity can be determined empirically using a suitable equation for Newtonian or non-Newtonian flow or from correlation using a calibration reference material which follows the same model under similar conditions. The measurement cycle of steps c) through f) can be consecutively performed to provide a more continuous insight into the viscosity or viscosity change of the fluid. Preferably, steps c) through f) are sequentially repeated under the control of a computer. The variation of viscosity can be affected by introduction of an oxidation gas in step c) under oxidative conditions: e.g. at a temperature from about 100° C. to 200° C., preferably 150° C. to about 180° C. The variation of viscosity can be continued until an oxidation breakdown parameter is determined, for example a relative viscosity increase (20%, 25%, 50% etc), a time period, or to preset viscosity limit, etc.

Another aspect is directed to a method for measuring viscosity or related rheological properties of a plurality of fluid samples comprising:

a) providing a plurality of fluid samples into individual reservoirs, wherein the reservoirs are placed under thermostatic control;

b) providing a plurality of capillary systems which provide a flow path for the fluid sample in a reservoir, each system having a capillary tube having a first end and a second end with a substantially uniform diameter over a predetermined length, the first end positionable and submerged in the fluid sample, the second end attached to a manifold having at least one selectable valve thereby defining a chamber of predetermined volume, the manifold having a pressure sensor;

c) actuating at least one selectable valve attached to the manifold on each capillary system to allow a gas to enter into and pass through the manifold and capillary;

d) switching the actuation in step c) and suddenly inducing the sample into the capillary by rapidly generating a dynamic differential pressure in the chamber thus allowing the sample to flow from the reservoir through the capillary;

e) detecting pressure change of the chamber as a result of the fluid flow; and f) relating the rate of pressure change to a theological property.

A capillary system can be employed in the method of the present invention. Thus, this aspect is directed to a method for measuring a relative increase in viscosity in a plurality of fluid samples comprising:

a) providing a plurality of fluid samples into individual reservoirs, wherein the reservoirs are placed under thermostatic control;

b) providing a plurality of capillary systems which provide a flow path for the fluid sample in a reservoir, each system having a capillary tube having a first end and a second end with a substantially uniform diameter over a predetermined length, the first end positionable and submerged in the fluid sample, the second end attached to a manifold having at least one selectable valve thereby defining a chamber of predetermined volume, the manifold having a pressure sensor;

c) actuating at least one selectable valve attached to the manifold on each capillary system to allow an oxidation gas to enter into and pass through the manifold and capillary;

d) switching the actuation in step c) and suddenly inducing the sample into the capillary by rapidly generating a dynamic differential pressure in the chamber thus allowing the sample to flow from the reservoir through the capillary;

e) detecting pressure change of the chamber as a result of the fluid flow; and f) relating the rate of pressure change to an apparent viscosity property.

BRIEF DESCRIPTION OF THE DRAWINGS

Other objects and many of the intended advantages of the present invention will be readily appreciated by reference to the detailed description in connection with the accompanying drawings.

DETAILED DESCRIPTION OF THE INVENTION

Figure 1:
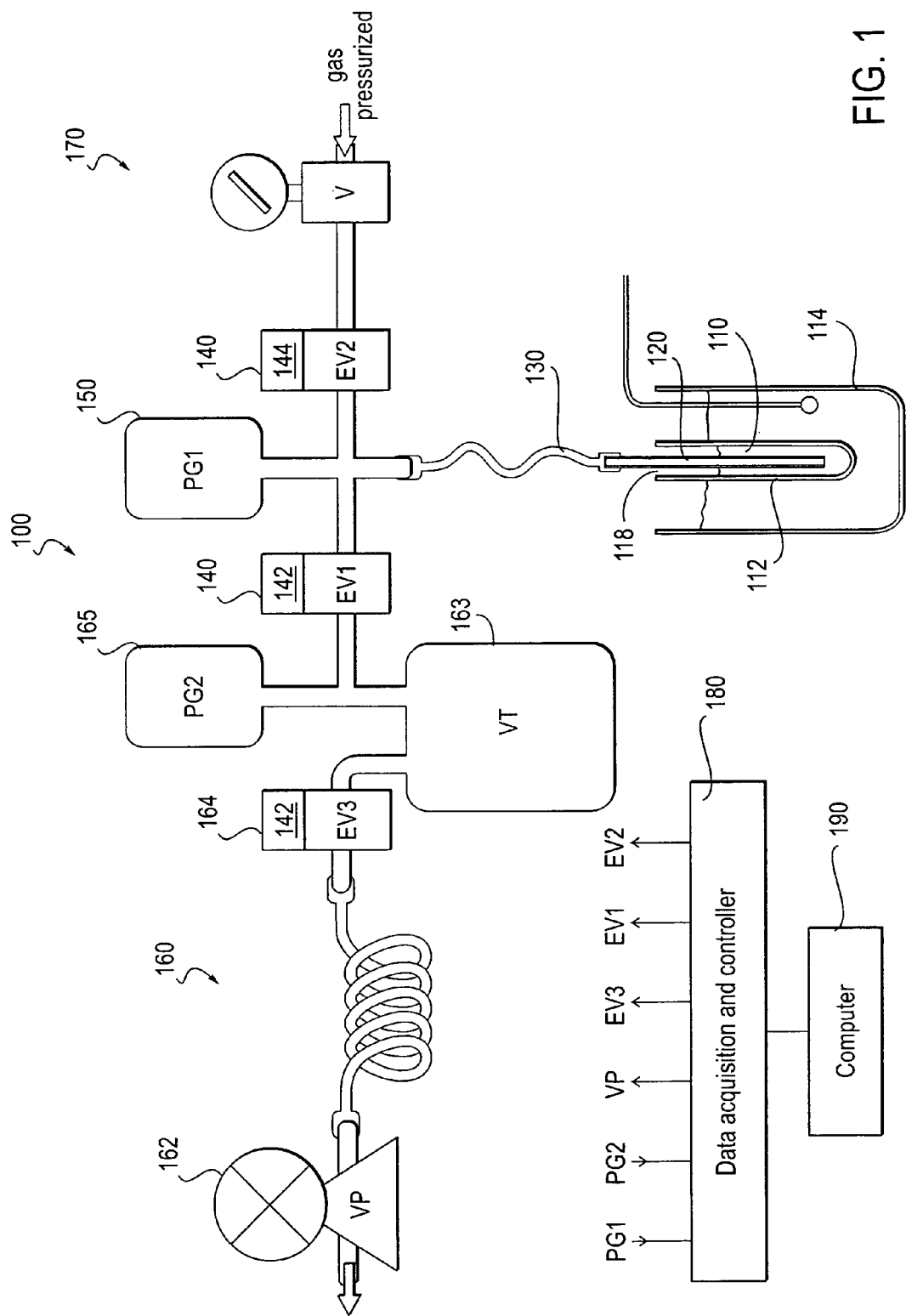
FIG. 1 is a schematic of the alternate pressure viscometer device

FIG. 1 shows a schematic plan of an apparatus which can be used for determining a rheological property of a fluid. It is particularly suited for determining a change in the flow of the test fluid by repeated evaluation of the test fluid over time and thus suitable for use in measuring viscosity as well as changes in viscosity. More specifically, in FIG. 1, the device 100 can be used to determine the dynamic viscosity of a test fluid 110. The device 100 includes a capillary 120 in communication with the test fluid 110 which is contained in a reservoir 112 placed in a thermostatic control system 114 used to regulate the temperature of the test fluid to a desired set point. Commercial thermostatic control systems are widely available, particularly suited temperatures are from about −35 degrees Celsius to about 200 degrees Celsius. The reservoir is charged with test fluid to be examined and placed in a thermostatic control system 114 to keep its temperature constant at least during the desired measurement period. Any thermostatic control system 114 can be used but it is preferred to use a system so designed that several reservoirs 112 can be charged therein at a time, to improve efficiency of operation. The reservoir 112 can be open to the atmosphere or sealed by a sealing member in conjunction with the capillary 120.

The capillary 120 provides a restriction to flow path and is selected to be a suitable length to mitigate end effects and of a cross section suitable to achieve laminar flow in the region. The capillary 120 is conveniently selected as being a long thin circular tube, commonly a needle. The capillary can also be selected such as to resemble a cylindrical annulus defining an annular region between two coaxial circular cylinders or a narrow slit formed by two narrow walls. Preferably, the capillary is a capillary tube.

The capillary 120 is connected by a manifold 130 to a selectable valve 140. The capillary 120 together with the manifold 130 and the valve 140 define a chamber of a predetermined volume. The volume of the chamber can be determined empirically, calculated, or by other suitable methods. In operation, the chamber receives a portion of the test fluid 110 which flows through the capillary 120 under the influence of a difference in pressure across the capillary system. The driving pressure can be positive pressure or vacuum, however it is important that the driving force be reproducible and relatively fast acting onto the chamber. The chamber is outfitted with a pressure sensor 150 which can be used to record the differential pressure in the chamber during a measurement cycle. The differential pressure can be output for data acquisition and control and to a computing device for recordation and further manipulation. The selectable valve 140 can be a single valve, such as for example a three way valve which conveniently can be in communication with a regulated pressure source 160, a second pressure source 170 and the pressure gauge 150. In a preferred aspect the regulated pressure source 160 and the second pressure source 170 are offset by more than one selectable valve 140 such as 142 EV1 which can be a normally closed electrovalve and 144 EV2 which can be a normally open electrovalve, wherein the electrovalves can be controlled by a data acquisition device and controller 180. The electrovalves are selected to be relatively fast acting valves, with valve actuation occurring in fractional seconds.

The pressure sensor device 150 converts said pressure measured to an electrical signal, typically a voltage or current capable or being converted to a digital signal for processing by a data acquisition and controller device 180. Typically the electrical signal output by the pressure sensor is a direct current voltage, being in the order of several volts. The output signal can also be direct current amperage, measured in milliamps. The pressure sensor can be used to measure differential pressure for example between the chamber and ambient pressure. The data acquisition and controller device 180 is used to convert the electrical signals to digital data for further computation with a computer 190, commonly a personal computer. Most typically, the conversion is analog to digital conversion. Modules combining data acquisition device, a control device and a computing device are commercially available.

The regulated pressure source 160 provides the motive force for inducing a test fluid 110 to flow through the capillary 120 and into the chamber. The regulated pressure source 160 is discontinuous in a test cycle, it is quickly applied to a predetermined setpoint to create a differential pressure which is dynamic and changes as test fluid 110 is induced into the chamber. Particularly preferred is a regulated reduced pressure source 160, such as a vacuum source. Regulation of the vacuum source may be accomplished by numerous methods known in the art. In one aspect, the reduced pressure source employs a vacuum pump 162 coupled to a vacuum tank 163 equipped with a vacuum tank pressure gauge 165. The vacuum tank is regulated around a set point by at least one vacuum tank selectable valve 164; typical set points are from −50 millibars to −150 millibars and have a desired precision from about +/−1 millibar around the set point. The vacuum tank pressure gauge 165 measures the vacuum in the vacuum tank 163, when this measure is greater than the desired precision, a controller 180 can open a vacuum tank selectable valve 164 and optionally commence operation of the vacuum pump 162 for a period of time until the vacuum regulation is within the desired precision. In a similar fashion if the vacuum tank is a pressure lower than the desired precision, a gas can be introduced into the vacuum tank.

A second pressure source 170 is coupled to at least one selectable valve 140 and used to evacuate the test fluid 110 from the capillary 120. The second pressure source is regulated in flow and pressure using suitable techniques. These parameters are not critical and selected under suitable conditions to induce the test sample to evacuate the capillary system and thus are selected with reference to the regulated pressure source 160. Typical parameters are around 0.5 bar (from about 0.1 bar to about 5.0 bar) and around 1.0 liter/hour (from 0.1 liter/hr to about 5 liters/hr). A convenient second pressure source 170 is selected from the group consisting of compressed gases such as air, nitrogen, oxygen, helium, $NO_x$ and the like. Particularly preferred is an oxidative gas and thus the test fluid 110 can be profiled by viscosity change in reference to oxidation. During operation, the second pressure source flow and pressure can be adjusted to slowly bubble a gas through the test fluid. In this method of operation, the device of the present invention can be used to study oxidative effects or the effects of nitration on a test sample or a battery of test samples. Thus, for example test samples may be evaluated for oxidative performance or nitro-oxidative performance in real time. In this aspect, the second pressure source 170 is integrated into the operation and serves the dual function of evacuating the test sample from the capillary and to serve as an oxidative gas source.

Figure 2:
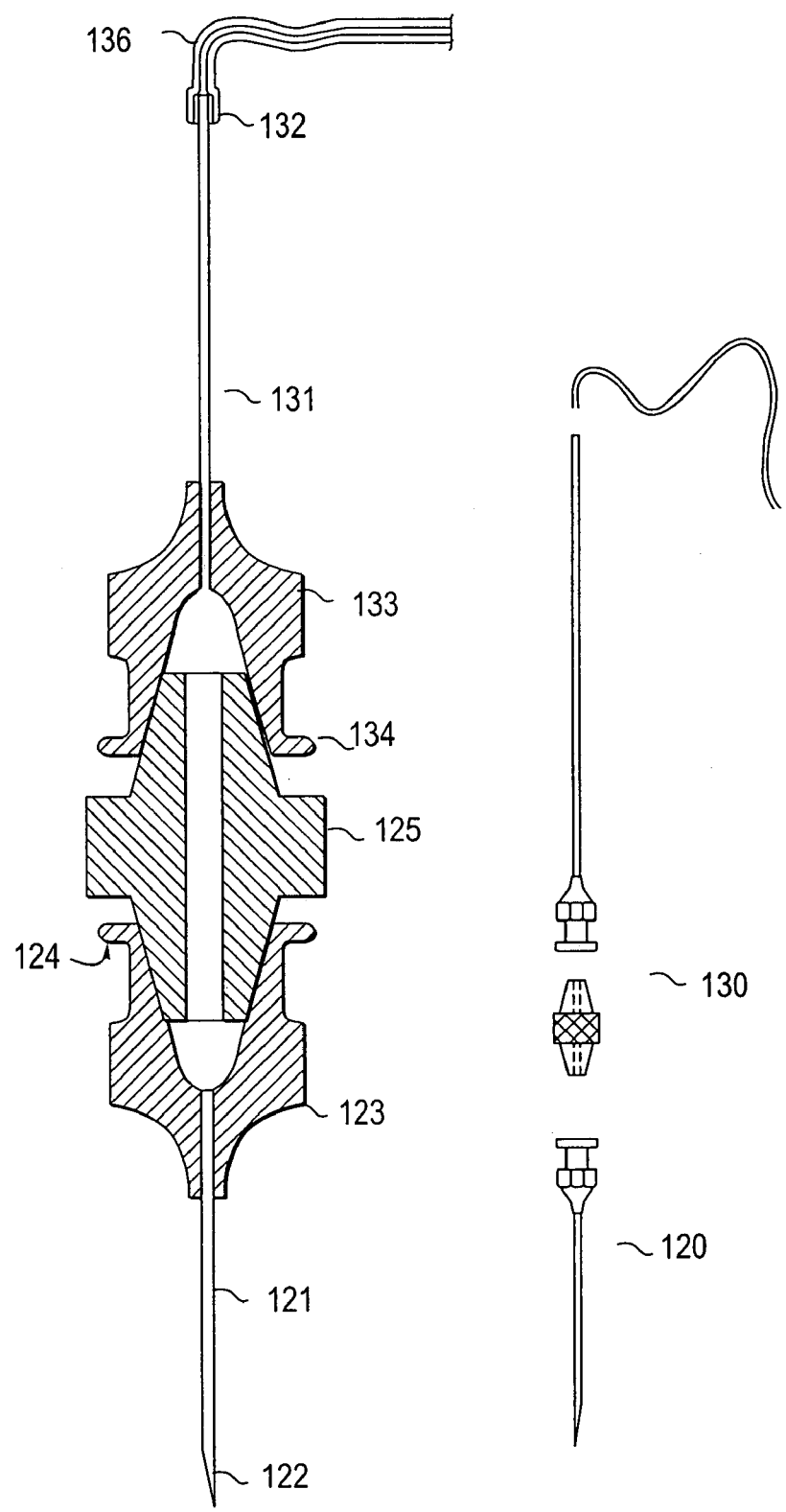
FIG. 2 shows a partial exploded view of the capillary comprising a syringe
Figure 3:
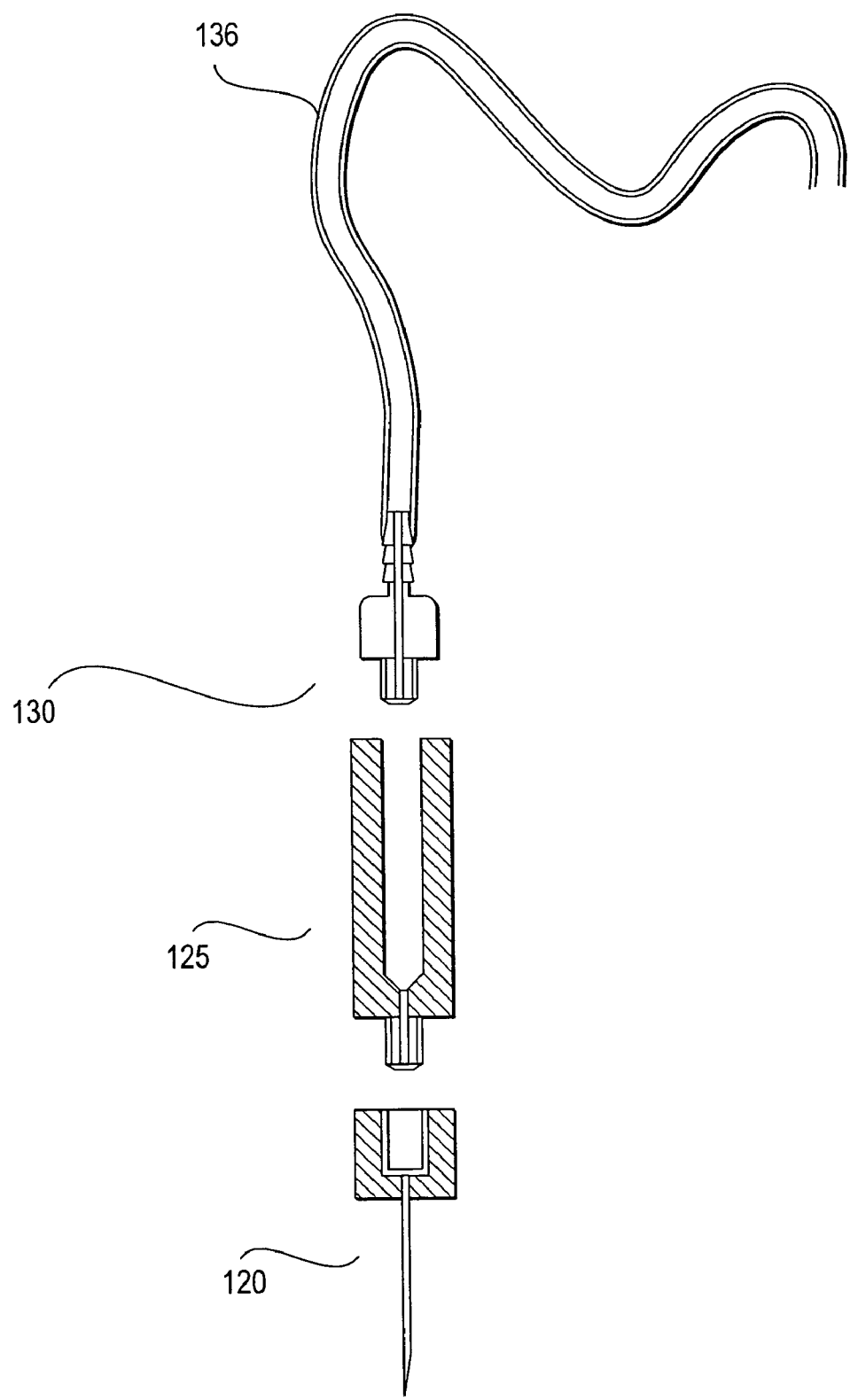
FIG. 3 show a cross sectional view of the capillary with connector

FIG. 2 shows a partial exploded view of the chamber 130 which includes the capillary cannula 120. The capillary includes a stainless steel hypodermic needle 121 which has a uniform diameter (d) over a predetermined length (l) with l>>d. On one end of the needle 121, it has a flat tip 122 which is positional and submersed in the test fluid 110 during a measurement. The size and length of the needle can be varied according to the expected fluid properties over the measurement. As shown in FIG. 2, a suitable needle is for example a 25 G, 1" long Luer. Common commercially syringe needles presented in gauge size for example Gauge 10 to Gauge 33, with the higher number referring to the smaller nominal inside diameter, preferably 15-30 G are selected. Typically, the needle has a selected to have a length of from between about 10 mm to about 100 mm with an inner diameter from bout 0.1 mm to about 1.5 mm. Thus suitable viscosities range from about 1 cP to about 10,000 cP. The diameter of the capillary tube is pre-selected in accordance with the test sample. The opposing end from the flat tip 122 has a standard Luer hub 123, which is used to connect the capillary 120 the manifold 130. The Luer hub 123 has a flanged head 124 which communicates with a connector 125 illustrated by a male/ male Luer connector. The other end of the connector 125 is attached to a similar needle 131, however illustrated in FIG. 2 is a 20 G, 6" long Luer. The tip end of this is attached to a tube 136 which ultimately attaches to at least one selectable valve 140, not illustrated. The internal volume for the manifold 130 including the capillary 120 is fixed by the selection of the components having the internal recesses and provides a flow path for the test fluid 110. FIG. 3 illustrates an alternative capillary and manifold arrangement indicating alternative connector member configurations. Numerous suitable connectors and fasteners are known in the art, including but not limited to Luer locks and Luer slip-ons, threaded connectors, connectors to tubing, etc. The connector 125 in FIG. 3 can be fabricated to have a larger internal volume for retaining a larger volume of test fluid 110 in a measurement cycle. This larger volume may also serve and prevent an aliquot of test fluid 110 from contaminating non-wetted areas of the manifold. It is particularly desirable to avoid contamination of sample to the regulated vacuum source. Also, advantageously the components which define the manifold are inexpensive and easily replaced. Thus, for example, these components could be single use or readily disposable if the test sample plugs and/or contaminates the components. Commonly in oxidation tests, the oxidation by-products contaminate the capillary tubes and are not readily cleaned.

Figure 4:
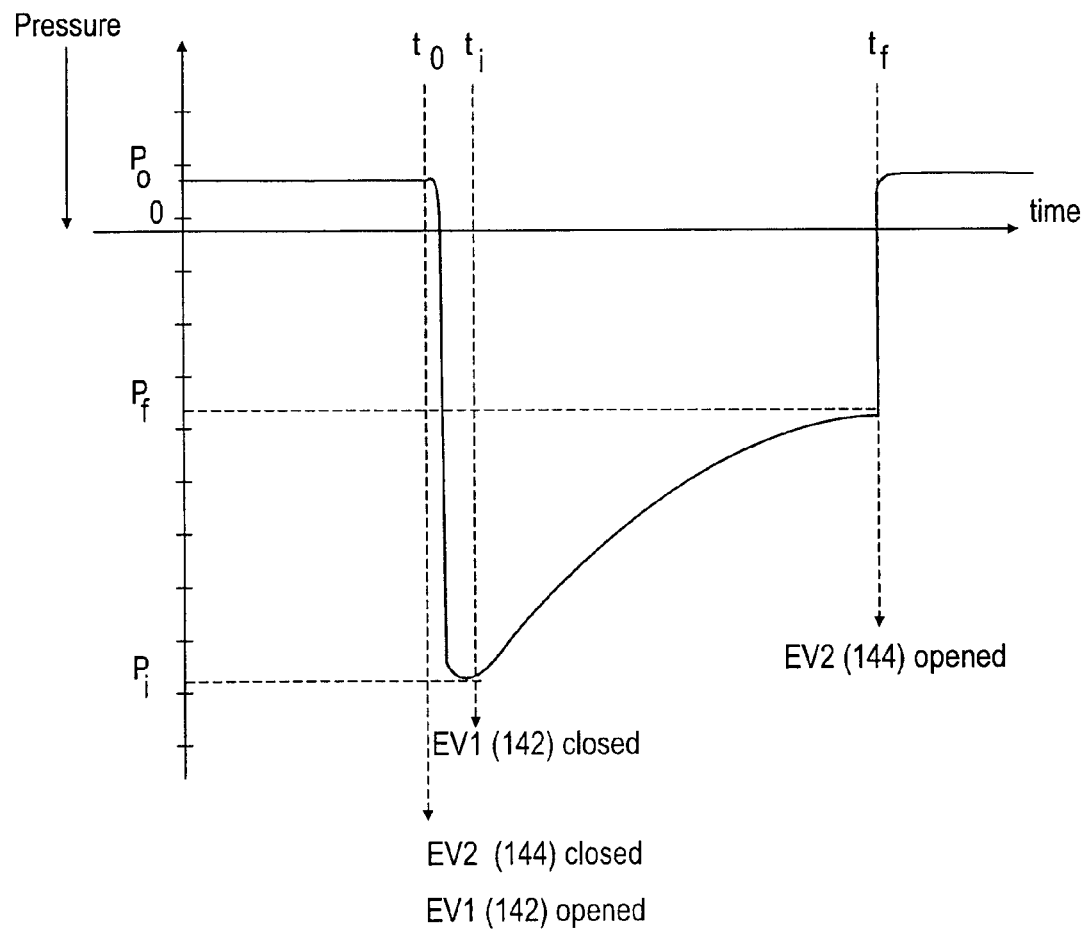
FIG. 4 is a plot of pressure verses time during a measurement cycle

FIG. 4 is a characteristic pressure vs time plot for a single measurement of the apparatus, indicating the various pressures in the chamber during the measurement cycle. Prior to commencing the cycle thus at time $t_o$ the chamber is at a pressure derived from the second pressure source 170, $P_o$ selected at a suitable pressure and flow rate suitable to evacuate the chamber and ready the device to a measurement. A regulated pressure source is suddenly applied to provide an external driving force to induce a test fluid into the capillary. The time frame between $t_o$ and $t_i$ is maintained to be a short duration so that $V_o$, the volume at time $t_o$ can be approximated as equivalent to $V_i$, the volume at time $t_i$, typically the duration is fractional seconds typically less than 0.5 and more preferably less than about 0.2 seconds. The volume $V_o$ is related to the designed capillary circuit total volume. At time $t_o$ the system is being readied for a measurement, and the selectable valves 140 are suitably positioned. For example EV2 144 is closed and EV1 142 is opened, thereby applying the regulated pressure source 160 the system to induce the test fluid 110 into the capillary 120. In FIG. 4, a reduced pressure $P_i$, the driving pressure differential related to a predetermined setpoint, is achieved and EV1 142 is closed. This rapid pressure change generates a pressure differential in the chamber which induces the test fluid into the chamber. The flow of the test fluid is illustrated from $t_i$ to $t_f$ where the pressure changes from $P_i$ to $P_f$ over the measurement. Typically the duration of the measurement cycle is less than a few seconds, preferably less than 10 seconds and typically around 5 seconds. At time $t_f$ indicating the end of the active measurement cycle, EV2 144 is opened allowing for the test sample to chamber and ready the system for a new measurement cycle. An advantage of this present system is that the measurement cycle can be repeated after time $t_f$ without further intervention. Thus for example momentarily after $t_f$ a new cycle can begin at a new $t_o$ after only a few seconds to fractional seconds of delay.

Figure 5:
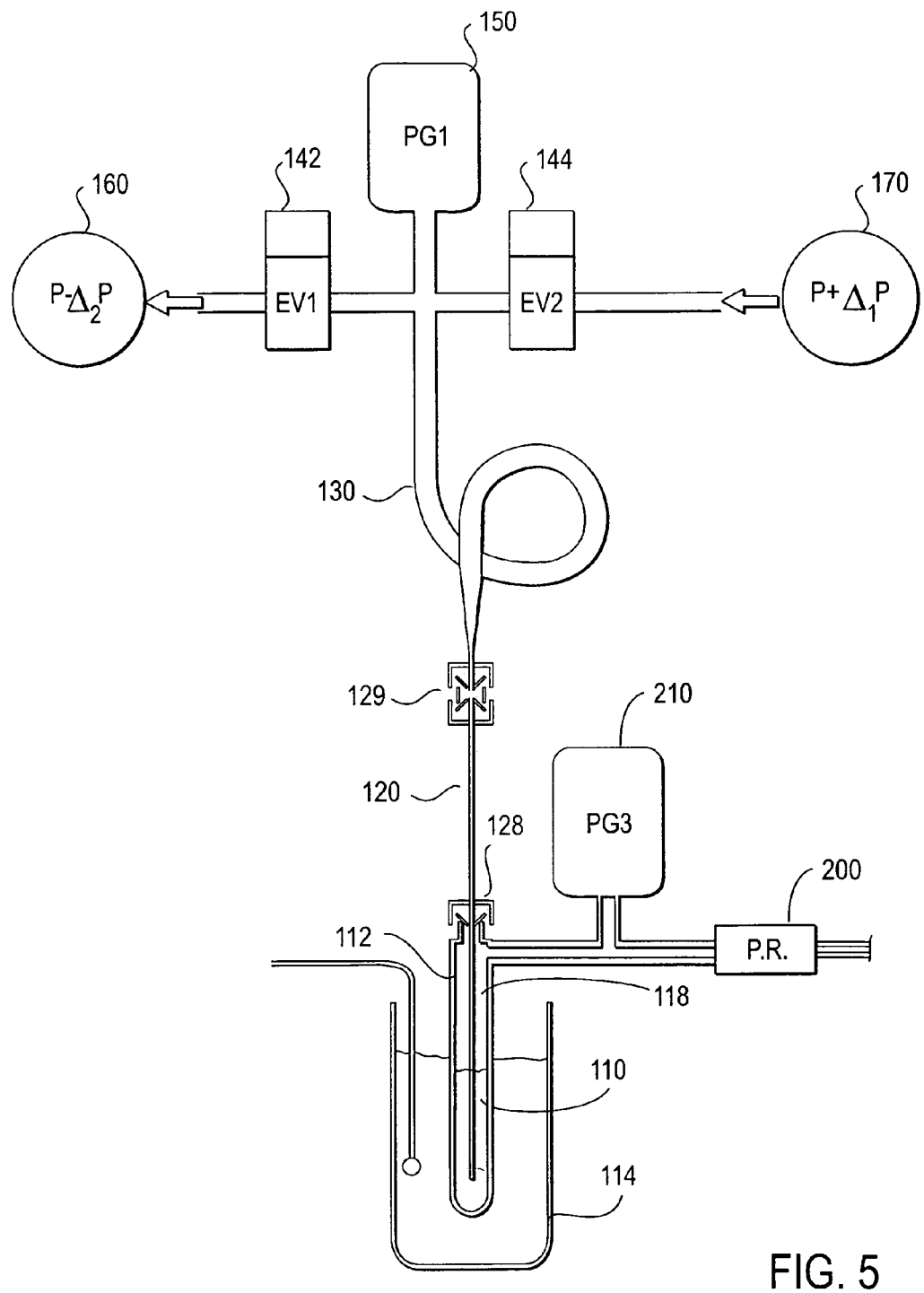
FIG. 5 is a partial schematic of the alternate pressure viscometer device employing a positive pressure to create an increasing pressure differential in measurement circuit

An alternate partial schematic configuration of the apparatus of the present invention is illustrated in FIG. 5. FIG. 5 employs a positive pressure driving head in the chamber 118 applied on the surface of the test sample. The test sample is placed into a sealed reservoir 112 by using a sealing member 128 which removably couples with the reservoir and/or the capillary 120. A further sealing member 129 can couple/decouple the capillary 120 to the manifold 130 to allow fluid communication there through. The reservoir can be pressurized, whereby the release of the pressure induces test sample 110 to flow into the capillary 120. The release of pressure may be effectuated via a valve to a lower pressure environment as illustrated in FIG. 5; this may be the regulated pressure source 160 or the second pressure source 170. The reservoir is placed into a thermostatic control system where temperature is maintained. The pressure differential is measured as the test sample flows through the capillary. The positive pressure driving head is pressure regulated 200 and controlled (not shown) to provide a reproducible and discontinuous motive force in the pressure chamber 118 to induce the test fluid 110 into the capillary 120. Alternatively, the positive pressure driving head may be applied by the second pressure source 170 through the manifold 130 and capillary 120 such that positive pressure driving head in the chamber 118 is regulated via the second pressure source 170, the pressure regulator 200 or in combination. The positive pressure driving head in the chamber 118 is monitored by a pressure gauge 210 and/or 150 to record the differential pressure in this chamber during the measurement cycle. FIG. 5 illustrates the second pressure source 170 at a driving pressure of $P+\Delta_1 P$ which is offset by electrovalves 144 and 142 from the regulated pressure source 160 and the manifold 130 which is in fluid communication with the test fluid through the capillary 120. The regulated pressure source 160 in this instance is preset at $P-\Delta_2 P$. The difference in these pressures from the second pressure source 170 and the regulated pressure source 160 in the sealed reservoir can provide positive pressure driving head in the chamber 118 to induce the test sample 110 to flow through the capillary. As described above, the rate of the pressure change in the time frame is able to determine a theological property of the fluid measured.

An apparatus employed in the method aspect of the present invention may comprise a capillary having a first end and a second end with a substantially uniform diameter over a predetermined length, the first end disposed for fluid communication with a liquid sample to be measured, the second end attached to a manifold having at least one selectable valve, the capillary together with the manifold and the at least one selectable valve define a chamber of predetermined volume, a regulated pressure source initially applied to induce the sample into the capillary and generate a differential pressure in the chamber, a pressure sensor attached to the chamber for outputting differential pressure to a computing device, and a second pressure source coupled to the at least one selectable valve for evacuating the sample from the capillary. In a preferred operation, as the liquid sample flows through the capillary, the differential pressure in the chamber is dynamic changing as the sample flows through the capillary and preferably this is a decreasing differential pressure and thus the regulated pressure source is a reduced pressure source for example derived from a vacuum device. The reduced pressure source may further comprise a vacuum pump, a vacuum tank, a pressure gauge and a control system to regulate the reduced pressure source around a defined setpoint.

In one aspect, the second pressure source is selected to be a pressure and flow rate suitable to allow the liquid sample to be measured to evacuate the capillary prior to a measurement cycle. A preferred second pressure source is a compressed gas at a pressure greater than the pressure of the regulated pressure source. In this aspect the compressed gas is selected from the group consisting of compressed gases such as air, nitrogen, oxygen, helium, $NO_x$. A particularly preferred compressed gas is an oxidative gas.

The apparatus is particularly suited to viscosity and/or viscosity changes. Thus one aspect is directed to a capillary viscometer for sequential measurements of a liquid sample comprising: a capillary having a first end and a second end with a substantially uniform diameter over a predetermined length, the first end disposed for fluid communication with the liquid sample to be measured, the second end attached to a manifold having at least two selectable valves, the capillary together with the manifold and the at least two selectable valves define a chamber of predetermined volume, the first valve in communication with a regulated reduced pressure source for inducing the sample into the capillary and chamber, a pressure sensor attached to the cavity for outputting differential pressure, a computing device coupled to the selectable valves and pressure sensor, and a second pressure source at a pressure suitable to evacuate the sample from the capillary. The capillary viscometer can further comprise a device to record the variation of pressure over a measurement. Furthermore a computing device can be used to process the pressure variation speed and equate to a theological property. Preferably the computing device is used to define a relationship between the pressure variation speed and viscosity using a reference fluid.

Another aspect is directed to measuring a plurality of fluid samples using a single apparatus, thus disclosed is an apparatus for measuring viscosity or related theological properties of a plurality of fluid samples, the apparatus comprising: a frame; a plurality of capillary systems which provide a flow path for the fluid samples, each system having a capillary tube having a first end and a second end with a substantially uniform diameter over a predetermined length, the first end positionable for fluid communication with a fluid sample contained in a sample holder, the second end attached to a manifold having at least one selectable valve thereby defining a cavity of predetermined volume, the manifold having a pressure sensor; at least one pressure source coupled to each capillary system through the selectable valve and adapted to induce the fluid sample into each capillary system at the beginning of a measurement and to evacuate the sample at the end of the measurement; an assembly attached to the frame for securing at least a portion of the capillary system; and a device for recording differential pressure in each manifold and relating the differential pressure to a fluid property. A preferable rheological property is viscosity.

The equations required in the calculation are derived from the following theoretical considerations, assuming that the product of the pressure in the chamber and the volume of uncharged space are constant, the Boyle-Mariotte relationship can be used to determine the total volume test fluid in the capillary and chamber at the end of the measure as illustrated in Equation 1

$$P_i V_i = P_f V_f \tag{1}$$

where $P_i$ is the initial pressure at the initial time $t_i$, $V_i$ is the initial volume at the initial time $t_i$; and likewise $P_f$ and $V_f$ are the pressure and volume at time $t_f$. Typically at time prior to $t_i$ (for example at time $t_o$) the system is at a second pressure source suitable to evacuate the capillary and chamber at thus the volume is preset by design as $V_{tot}$. From knowing the total volume of the circuit and the pressures during the measurement, the volume of sample induced into the capillary and chamber can be determined. Likewise if desired, the flow rate of the test fluid Q could be determined from Q=dV/dt. Particularly, by defining the flow parameters as steady-state, isothermal and laminar using a capillary of known dimensions, a functional dependence exists between the volumetric flow and the pressure drop due to friction. From the volume of the fluid displaced and a known characteristic of the system (internal diameter and length of the capillary, pressure values, test duration, flow characteristics, etc) the Hagen-Poiseuille equation can be used to define the rheological properties of the fluid, more specifically the viscosity, shear rate and shear stress. This equation illustrates the relationship between the volume rate of flow and the forces causing the flow and is particularly relevant by systems defined for systems having a Reynolds number less than about 2300.

The Hagen-Poiseuille equation can be used to model the flow considering a fluid element in the capillary tube by derivation of relationship of the pressure drop at the capillary as a function of capillary tube geometry, fluid viscosity and flow rate. Accordingly, Equation 2:

$$\mu = \frac{\pi R^4 \Delta P t}{8 L V} \tag{2}$$

where: $\mu$ is the Newtonian apparent viscosity, R is the radius of the capillary, L is the length of the capillary, t is time measured of the interval, $\Delta P$ is the pressure measurement over the interval and V is volume measured over the interval. In a similar fashion the shear stress and the shear rate can be determined. The shear stress at the tube wall can be obtained as illustrated in Equation 3 with the shear rate illustrated in Equation 4:

$$\tau_w = \frac{R \Delta P}{2L} \tag{3}$$

$$\gamma_w = \frac{4Q}{\pi R^3} = \frac{4V}{\pi R^3} \tag{4}$$

where $\tau_w$ is the shear stress at the capillary wall, $\gamma_w$ is the wall shear rate, Q is the volumetric flow rate.

In a more pragmatic way, a function between the dynamic viscosity (cP) and the variation of the pressure vs time (mb/s) relationship can be defined using a set of adapted calibration products. Known viscosity of reference samples can be used to calibrate the system under specific set of conditions. Using the device of the present invention the pressure variation speed ($P_v$) can be measured and stored by a data acquisition device for use in defining a relationship between the pressure variation speed and the viscosity. Numerous mathematical models can be employed to describe this relationship, such as using the method of least square to fit the curve to define $\mu = f(P_v)$ or using geometric mean values, etc. The generated coefficients are stored, typically in a computer, and accessed to define the viscosity of an unknown sample from this relationship. Even without calibration, the relative viscosity change can be determined using repeat measurements.

For Newtonian fluids the viscosities are independent of shear rate, thus $\gamma_a = \alpha \tau_w$ or $\gamma_w = \mu \tau_w$. For non-Newtonian fluids, the viscosities of the test samples will vary with shear rates. Numerous acceptable models have been used to define these behaviors. For example, for power law fluids, the apparent shear rate is related to the shear stress by $\gamma_a = (\alpha \tau_w)^{1/n}$ and thus $\mu = (4n/(\alpha(3n+1)))_n (\gamma_a)^{n-1}$ and $\gamma_w = \alpha((3n+1)/4n)\tau_w^{1/n}$ where n is a power law exponent. If the liquid behaves as a Bingham fluid, the apparent shear rate is related to the shear stress by $\gamma_a = \alpha(\tau_w - \tau_{B1})$ where $\tau_{B1}$ is given from the yields stress relation $\tau_r = (3/4)\tau_{B1}$ and thus $\mu = 1/\alpha$ and $\gamma_w = \alpha(\tau_w - 3\beta/4)$. If the liquid behaves as a Casson fluid, the apparent shear rate is related to the shear stress by $\gamma_a^{1/2} = \alpha(\tau_w^{1/2} - \tau_{CA})$ where $\tau_r = (49/64)\tau_{CA}^2$ and thus $\mu = a^2$ and $\gamma_w^{1/2} = (\tau_w^{1/2} - \tau_{CA})/\alpha$, where $\tau_{CA}$ is the Casson yield stress.

In the study of lubricants and lubricating oils, oxidation is an important phenomenon that needs to be controlled to increase oil drain intervals for engine oils and maintain good lubrication of the engine during the whole length of the drain interval. Many engine tests have been and are being developed to reproduce this phenomenon and qualify engine oils with adequate performance. These engine tests are long, expensive and require big amounts of test lubricant, which produce a lot of waste.

In order to classify the performance of new lubricants, additives, and formulations; it has been imperative to develop improved laboratory tests for predicting and simulating actual engine tests response more expeditiously with improved response, in less time and with less sample. Numerous laboratory oxidation tests have been developed for many years for this purpose, but even though they use less amount of test oil, they still require several days of testing, use around 100 g of test oil and require regular sample taking to be able to follow the oxidation reaction over time. Most of the existing oxidation tests require sampling to be able to follow the evolution of key parameters such as viscosity, oxidation, and/or nitration IR peaks, TAN, metals concentration and the like. Removal of the sample for quantification during the test is difficult and changes concentration in the bulk sample, thus many methods only take a sample at the end of the test. Some other methods follow the evolution of oxygen pressure in a closed reactor (rotary bomb oxidation test, TFOUT, etc.). Typically the inhibition period is determined from measurement of oxygen absorption (e.g. in an oxidation bomb apparatus), heat of reaction (e.g. DSC), formation of reaction products (e.g. acids, peroxides, insolubles, gaseous products) and/or change in physico-chemical properties such as increase in viscosity. However, a common feature to these tests is the need for big and costly equipment and the need for handling the samples, the method aspect of this invention overcomes this problem. An aspect of the method of the present invention can be used to screen and/or evaluate the antioxidant capabilities of base oils, engine oils, and lubricating oil additives by determining the relative viscosity increase in the presence of oxidation conditions.

The alternate pressure viscometer of the present invention can be employed to provide a rapid analysis of the relative increase of viscosity in a myriad of test conditions, such as high temperature oxidation/nitration curves, dispersivity study, thermic shear of VII etc. One feature of the device of the present invention is that it is able to measure in-situ the oil viscosity during an oxidation and provide viscosity measurements in-succession and without undue interruption since the measurement cycle is automated and short.

The alternate pressure viscometer of the present invention can also be employed to quickly provide the Viscosity Index (VI) of a liquid using at least two different temperature reference points. Petroleum oils have different rates of change of viscosity with temperature. The VI is a method of representing this change, based upon comparison with the relative rates of change of two arbitrarily selected types of oil that differ widely in this characteristic. A high VI indicates a relatively low rate of change of viscosity with temperature. Conversely, a low VI indicates a relatively high rate of change of viscosity with temperature. A method for measuring the VI of an oil is described in ASTM D 2270 incorporated herein by reference. Typically the VI scale is an empirical one based upon the arbitrary assignment of VI values to two different crude oils, commonly by measuring kinematic viscosity at 40° C. and 100° C. The viscosity temperature relationship of a Pennsylvania crude was arbitrary assigned a VI of 100 and the same relationship of a Gulf Coast crude was assigned a value of 0.

The device of the present invention can be utilized to measure an oil sample at two controlled temperatures for example at 40° C. and 100° C., determine kinematic viscosity from the measured pressure variation rate, as described herein above, and calculating the Viscosity Index using data from published table that are stored in a computer or by extrapolating such data.

EXAMPLES

The following examples were performed to demonstrate the performance of the device of the present invention.

Example 1

This example illustrates operation of the device using a single capillary system depicted in FIG. 1 and discloses a method for calibration of the apparatus using samples of known viscosity to generate a correlation between the pressure difference vs time measured in chamber as a function to the samples viscosity. The method indicated was used to calibrate a single capillary system, if a multi channel capillary was used; the calibration would be performed for each channel. Additionally, if the operational conditions were modified, for example, if the same capillary system was to be used with different values of reduced pressure, or measurement duration, or temperature, it would be necessary to calibrate again the system taking account for this new set of parameters.

In this example, four petroleum oils were selected which were representative of the range of viscosity chosen to study. More particularly four polyalphaolefin (PAO) oils were chosen: PAO2, PAO4, PAO5 and PAO7. Polyalphaolefins are manufactured by the oligomerization of linear alpha olefins (commonly 1-decene or 1-dodecene) followed by hydrogenation to remove unsaturated bonds and fractionation to obtain the desired product slate. PAO's are commonly categorized by numbers denoting the approximate viscosity in centistokes at one hundred degrees Celsius. The Kinematic viscosities (cSt) at 100° C. of these products were measured with a Hubbelhod viscometer according to the ASTM D445 and transformed in dynamic viscosity (cP) by using the density of each oil (cP=cSt*density).

The capillary system employed was similar to the capillary system depicted in FIG. 2. Here we use a system made with a Luer needle gauge 25 G-1" as the capillary, a male/male Luer splice and a second Luer needle gauge 20 G-6". This latter needle is spiced to the electrovalve circuit with 12 cm of a silicone tubing (internal diameter 0.5 mm), see FIG. 2. The 25 G-1" needle was selected to measure viscosities between around 1 cP and 10 cP. If other ranges of viscosity are to be studied, the needle and measure parameters may have to be modified. The capillary needles have generic length, for the range 8-25 cP and 3,000-10,000 cP the standard needle was cut to obtain the desired length; the value of the corresponding capillary length is indicated from the measure of the tip portion. The area between 25 cP and 3,000 cP was not included in the initial study but sets of parameters could easily be determined. TABLE 2 gives a set of parameters for three ranges of viscosities studied in this example, namely: 1 to 10 cP, 8 to 25 cP and 3,000 to 10,000 cP. These values were chosen for convenience to test the invention over various ranges of viscosity; these parameters are not intended to limit the invention or the working scope of the invention. For example, for a given range of viscosity with the other parameters being equal, a capillary having a smaller internal diameter of the needle will likely lead to a higher driving pressure and/or longer period for the sample. Numerous values and parameters can be defined and optimized.

The viscosity ranges and parameters set forth in this example allow quick access to study the flow characteristics and allows formulator to study simulated flow regimes encountered in monograde and multigrade engine oils according to the ASTM D445 and ASTM D5293 requirements needed in the SAE-J300. This kind of formulation data often requires three, four or more pre-blends before reaching the right viscosities, and even if the last measures have to be done in ASTM conditions, a lot of time can be gained by using this invention for the pre-blends. For example, using the device of the present invention approximately 6 minutes including the temperature stabilization is sufficient to get an average of three or four values. This compares to around 15 minutes for a single measure with the Cold Cranking Simulator (ASTM D5293) or around 20 minutes for a Hubbelhod viscometer (ASTM D445).

The device was set-up using an apparatus as illustrated in FIG. 1 wherein the sample to be tested was placed in a reservoir (open to ambient air) and placed into a temperature control bath. The capillary system was positioned so that the tip of the needle was below the surface of the sample. A 0.5 bars regulated compressed air source was attached, and the flow rate of 1 liter per hour allows bubbles to emerge from the tip of the syringe and to evacuate any sample. The reduced pressure motive force was secured by using a vacuum pump controlled and coupled to a 5 liter vacuum tank, the vacuum set point was set at −110 millibar+/−0.5 millibar and the test measurement cycle was set at 5 sec. The reduced pressure source was controlled by electrovalves. The electrovalves used in the system are solenoid-operated 2 or 3-way pinch valves, 24 VDC, coupled to the chamber using silicon tubing with an internal diameter of 0.8 mm (1/32"). A quick acting valve is desirable; the response time for these EV's is between 5 and 20 msec. The relative pressure gauges used for the reduced pressure control and the measure of the pressure variation speed have a range of 0 to −300 mbar for an analogical output of 0-10 VDC.

Software and hardware for the control of the process and the signal acquisition are from National Instrument Company (Austin, Tex.): LabVIEW™ for the software and field point modules for input/output signal, with the final data sent to an Excel spreadsheet. The process is largely automatic; the operator places the oil in the reservoir, the reservoir is placed in the thermostatic bath and starts the process. At the end of the process, the reservoir has to be removed and cleaned. An auto-sampler could easily be used to make measurements one after the other automatically for number of products in different reservoirs. Commonly robotic samplers can be fitted with one or more capillary systems to sample a single reservoir or to multiple reservoirs, either simultaneously or in rapid serial mode. Numerous robotic samples are known in the art and commercially available, suitable three axis robots are disclosed for example in U.S. Pat. Nos. 5,476,358 and 5,234,163. According to the capillary used and range of viscosity studied, the software program allows modifying the set point for the pressure, the time for applying the reduced pressure, the measurement duration, the time between two measurements, and the coefficients of the equation µ=f(P) explained below.

Measure: approximately 3 milliliters of PAO were placed in an open ended (to ambient air) reservoir which was allowed to equilibrate in a constant temperature silicone bath (or dry aluminum bath) at 100° C. degrees Celsius. The capillary was positioned to have at least one end immersed into the fluid, and then the flow rate of air was set to assure that air was bubbling in the PAO. The system was allowed to equilibrate for a period of time until the oil temperature in the reservoir is stabilized at 100° C. Due to the small quantity of oil in the reservoir, typically around 5 minutes are sufficient. To begin the measurement cycle, the regulated reduced pressure is quickly applied to the capillary and chamber to allow sample to begin to flow into the capillary tube. The reduced pressure is applied by action on the adapted electrovalve during 0.3 seconds and during the following 5 seconds the pressure variation over time is recorded. The acquisition rate is fixed to 10 values per second, the 50 values recorded look like a light curve; the computer is employed to process a linear regression on these 50 values, the slope of this line is used to define the mean of the pressure variation speed ($P_v$) in mb/s. After approximately 5 seconds of measure, compressed air is applied to empty the viscometer. Typically only a few seconds are required before the air bubbles again in the oil, for example here we waited approximately 10 seconds. To increase the precision of the test we repeated the measurement cycle three times and the average of the three pressure variation speeds was calculated. The reservoir was removed from the bath and the parts were rinsed with a solvent like heptane and dried before the next oil is measured according to the same procedure describe above.

Figure 6:
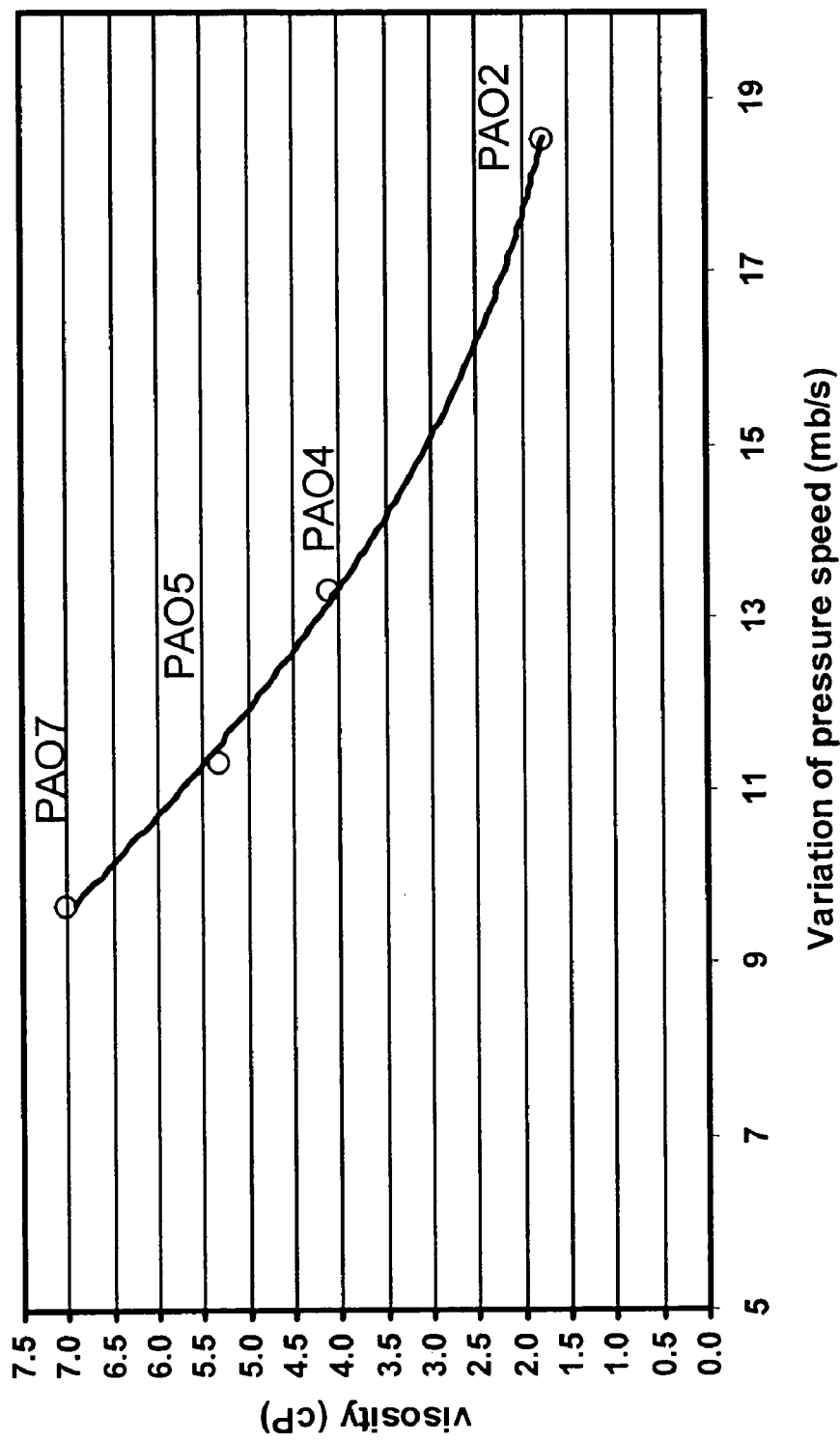
FIG. 6 is a plot of the function of viscosity with regard to a pressure vs time relation generated on polyalphaolefin samples using the alternate pressure viscometer device

After measuring the four PAO samples, the viscosities (µ) and the Pressure variation speed ($P_v$) are stored. Using this data and mathematically manipulating for example using the method of least squares, the equation $µ=f(P_v)$ is defined (TABLE 1 and FIG. 6). The coefficients of this equation are stored in the computer and are then used in the program to directly give the viscosity of an unknown product.

TABLE 1 calibration for a viscosity range 1 to 10 cP

| | Pressure variation speed (mb/s) | Viscosity µ (cP) |
|---|---|---|
| PAO2 | 18.56 | 1.760 |
| PAO4 | 13.36 | 4.1 |
| PAO5 | 11.36 | 5.300 |
| PAO7 | 9.72 | 7.000 |

$µ = 0.0427P^2 − 1.7914P + 20.301$

Example 2

This example is a presentation of some sequences of measures done on several petroleum products. The data demonstrates the repeatability of the device of this invention when it is employed to measure viscosity. These measures have been done with the single capillary system and according to the procedure and calibration method described in Example 1. The specific parameters for the capillary systems employed in this example are set forth in Table 2.

TABLE 2

Set of parameters

| | Viscosity range | | |
|---|---|---|---|
| | 2 to 10 cP | 8 to 25 cP | 3000 to 10000 cP |
| Internal diameter of the needle (mm) | 0.26 (25 G) | 0.41 (22 G) | 0.84 (18 G) |
| Length of the needle | 1" | 10 mm | 10 mm |
| Starting pressure (mb) | −110 | −90 | −220 |
| Measure duration (s) | 5 | 2 | 5 |

The device and parameters were not optimized; accordingly the values of repeatability described below have to be considered as the minimum of performance for the ability of this invention. Repeatability has been demonstrated for two ranges of viscosity 1-10 cP and 3,000-10,000 cP.

Results:

Range 1-10 cP

Four petroleum base oils have been chosen, which belong to the four main groups defined by API and ATIEL BASE STOCK CATEGORIES and cover the studied viscosity area:

PAO 2: Polyalphaolefin GROUP-4
Chevron RLOP 100N: Mineral oil GROUP-2
Total 150N: Mineral oil GROUP-1
Chevron UCBO-7R: Mineral oil GROUP-3

20 measures have been done sequentially for each product with the same parts and the same procedure described in Example 1. TABLE 3 shows the results and the statistics evaluation.

TABLE 3

Results and statistics data range 1-10 cP

| Range<br>1-10 cP (100° C.) | GROUP-4<br>PAO2 (cP) | GROUP-2<br>100N (cP) | GROUP-1<br>150N (cP) | GROUP-3<br>UCBO 7R<br>(cP) |
|---|---|---|---|---|
| 1 | 1.780 | 3.932 | 5.592 | 6.980 |
| 2 | 1.769 | 4.008 | 5.436 | 6.953 |
| 3 | 1.757 | 3.966 | 5.448 | 6.977 |
| 4 | 1.787 | 3.958 | 5.439 | 6.948 |
| 5 | 1.748 | 4.043 | 5.445 | 6.902 |
| 6 | 1.777 | 3.967 | 5.437 | 7.013 |
| 7 | 1.769 | 4.002 | 5.442 | 6.859 |
| 8 | 1.774 | 4.021 | 5.413 | 6.927 |
| 9 | 1.784 | 4.018 | 5.464 | 6.852 |
| 10 | 1.788 | 4.024 | 5.548 | 6.953 |
| 11 | 1.756 | 4.056 | 5.433 | 6.926 |
| 12 | 1.774 | 4.015 | 5.425 | 6.972 |
| 13 | 1.766 | 4.066 | 5.446 | 6.902 |
| 14 | 1.776 | 3.957 | 5.565 | 6.904 |
| 15 | 1.800 | 3.983 | 5.429 | 6.840 |
| 16 | 1.746 | 3.986 | 5.469 | 6.899 |
| 17 | 1.777 | 4.025 | 5.537 | 6.945 |
| 18 | 1.789 | 4.002 | 5.471 | 7.001 |
| 19 | 1.804 | 3.936 | 5.451 | 6.983 |
| 20 | 1.751 | 3.986 | 5.473 | 6.982 |
| Average | 1.774 | 3.998 | 5.468 | 6.936 |
| Degrees of freedom (dof) | 19 | 19 | 19 | 19 |
| Variance | 0.000268 | 0.001414 | 0.002581 | 0.002490 |
| Standard deviation | 0.0164 | 0.0376 | 0.0508 | 0.0499 |
| K student (0.025 – dof = 19) | 2.093 | 2.093 | 2.093 | 2.093 |
| Repeatability (single measure) (cP) | 0.048 | 0.111 | 0.150 | 0.148 |
| Repeat. (average of 2 measures) (cP) | 0.034 | 0.079 | 0.106 | 0.104 |
| Repeat. (average of 3 measures) (cP) | 0.028 | 0.064 | 0.087 | 0.085 |

As used herein the following terms are defined to mean:

"Repeatability (single measure)" means: The difference between two single measures done on the same product in the same conditions by the same operator will be different of 0.048 cP (example for PAO2) only in one case out of twenty.

"Repeat. (Average of 2 measures)" means: The difference between the average of two measures done on the same product in the same conditions by the same operator will be different of 0.034 cP (example for PAO2) only in one case out of twenty.

"Repeat. (Average of 3 measures)" means: The difference between the average of three measures done on the same product in the same conditions by the same operator will be different of 0.028 cP (example for PAO2) only in one case out of twenty.

Range 3,000-10,000 cP

One petroleum base oil, a Bright Stock Solvent, was measured 20 times at 5 different temperatures (2.5° C., 5° C., 7.5° C., 10° C. and 12.5° C.) to cover the range of viscosities between 3,000 cP and 10,000 cP.

TABLE 4

Results and statistics data, range 3,000-10,000 cP

| Range<br>3,000-10,000 cP | BSS<br>2.5° C. | BSS<br>5° C. | BSS<br>7.5° C. | BSS<br>10° C. | BSS<br>12.5° C. |
|---|---|---|---|---|---|
| 1 | 10944 | 8790 | 6651 | 4854 | 3153 |
| 2 | 11058 | 8859 | 6715 | 4785 | 3163 |
| 3 | 10994 | 8809 | 6740 | 4807 | 3186 |
| 4 | 10960 | 8753 | 6785 | 4801 | 3200 |
| 5 | 10994 | 9137 | 6777 | 4775 | 3184 |
| 6 | 10978 | 8886 | 6851 | 4785 | 3192 |
| 7 | 10932 | 8835 | 6737 | 4835 | 3180 |
| 8 | 11059 | 8957 | 6753 | 4844 | 3173 |
| 9 | 10963 | 8982 | 6646 | 4771 | 3186 |
| 10 | 11170 | 8974 | 6702 | 4838 | 3181 |
| 11 | 10799 | 8926 | 6645 | 4870 | 3224 |
| 12 | 10971 | 8733 | 6601 | 4837 | 3185 |
| 13 | 10984 | 8839 | 6808 | 4718 | 3180 |
| 14 | 10714 | 8889 | 6651 | 4843 | 3178 |
| 15 | 10853 | 9035 | 6715 | 4831 | 3188 |
| 16 | 10914 | 8926 | 6740 | 4814 | 3216 |
| 17 | 11127 | 8673 | 6785 | 4839 | 3222 |
| 18 | 10934 | 8696 | 6777 | 4862 | 3197 |
| 19 | 10922 | 8586 | 6851 | 4893 | 3200 |
| 20 | 10883 | 8994 | 6737 | 4818 | 3209 |
| Average | 10958 | 8864 | 6733 | 4821 | 3190 |
| Degrees of freedom (dof) | 19 | 19 | 19 | 19 | 19 |
| Variance | 10704 | 18189 | 4783 | 1631 | 335 |
| Standard deviation | 103 | 135 | 69 | 40 | 18 |
| K student (0.025 – dof = 19) | 2,093 | 2,093 | 2,093 | 2,093 | 2,093 |
| Repeatability (single measure) (cP) | 306 | 399 | 205 | 120 | 54 |
| Repeat. (average of 2 measures) (cP) | 217 | 282 | 145 | 85 | 38 |
| Repeat. (average of 3 measures) (cP) | 177 | 230 | 118 | 69 | 31 |

Example 3

Oxidation Test

The following study has been done with an eight channel capillary system. It differs from the single channel capillary system in the sense that the reduced pressure part is common for the eight capillaries so the measures have to be done one after the other. At the opposite, the gas pressurized part is unique for each cell and thus, there was a requirement to splice eight flowmeters. Here we used 150 mm flowmeters with a stainless steel ball for a range of 0 to 5 Liter per hour. The gas used for this example is air.

The oxidation performance of two passenger car engine oils is studied here. Each oil has been tested four times. A sequence of the eight measures of viscosity is done every 5 minutes. From the recorded values we calculate the percent of variation of the viscosity. The test is done at a temperature of 180° C., the air was bubbled in the oil at a flowrate of 1 l/h to commence suitable oxidation conditions. The test is stopped when the relative viscosity increase reached around 20 percent. TABLE 5 gives a summary of the parameters for this example.

TABLE 5

| Example 3 parameters | |
|---|---|
| Oil quantity | 3 ml |
| Catalyst | no |
| Gas | air |
| Gas pressure | 0.5 b |
| Gas flow | 1 l/h |
| Temperature | 180° C. |
| Reduced pressure | −110 mb |
| Internal diameter of the needle | 25 G |
| Length of the needle | 1" |
| Time to apply vacuum | 0.3 s |
| Measure duration | 5 s |
| Time between two serial of eight measures | 5 mn |

Figure 7:
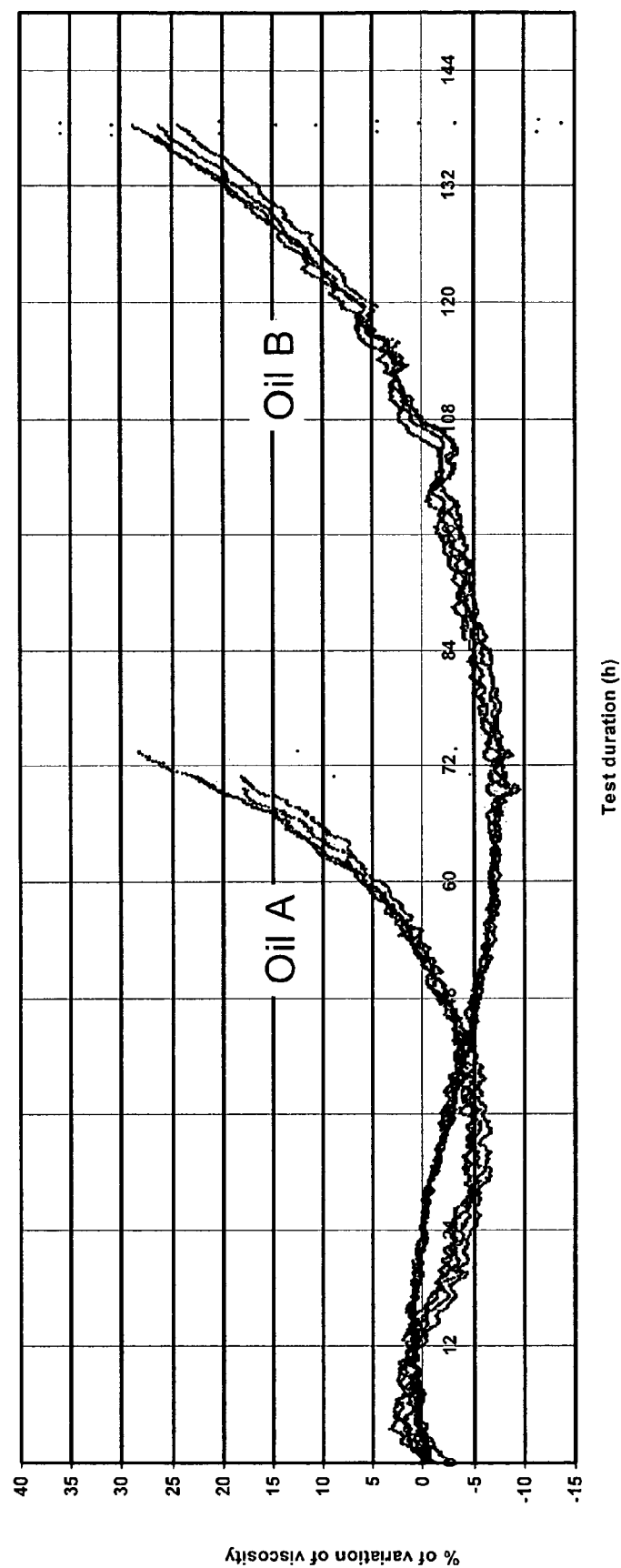
FIG. 7 is a plot of variation of viscosity in % over the test duration in hours generated by the alternate pressure viscometer device for two oils undergoing oxidation at high temperature

FIG. 7 shows the eight recorded curves demonstrating the oxidation curve generated for reference oil A and reference oil B illustrated in a plot of the % of variation of viscosity plotted against the cumulative time of the test.

Example 4

We used the same device as configured in Example 3; however a different secondary pressure source was used to illustrate the ability to use gas other than air for an oxidation test. Here, $NO_2$ was selected as oxidative gas to test the nitro-oxidation performance of Natural Gas Engine Oils (NGEO). Two internal low and high NGEO reference oils are tested. Oil A is the low reference and Oil B is the high reference. Only two capillaries have been used for this test, the six remaining capillary systems were disconnected. TABLE 6 gives details of parameters for this example.

TABLE 6

| Example 4 parameters | |
|---|---|
| Oil quantity | 3 ml |
| Catalyst 1: Naphtenate of iron | 75 ppm |
| Catalyst 1: Naphtenate of copper | 75 ppm |
| Gas | NO2 |
| Gas pressure | 0.5 b |
| Gas flow | 2 l/h |
| Temperature | 150° C. |
| Reduced pressure | −110 mb |
| Internal diameter of the needle | 25 G |
| Length of the needle | 1" |
| Time to apply vacuum | 0.3 s |
| Measure duration | 5 s |
| Time between two serial of eight measures | 5 mn |

Figure 8:
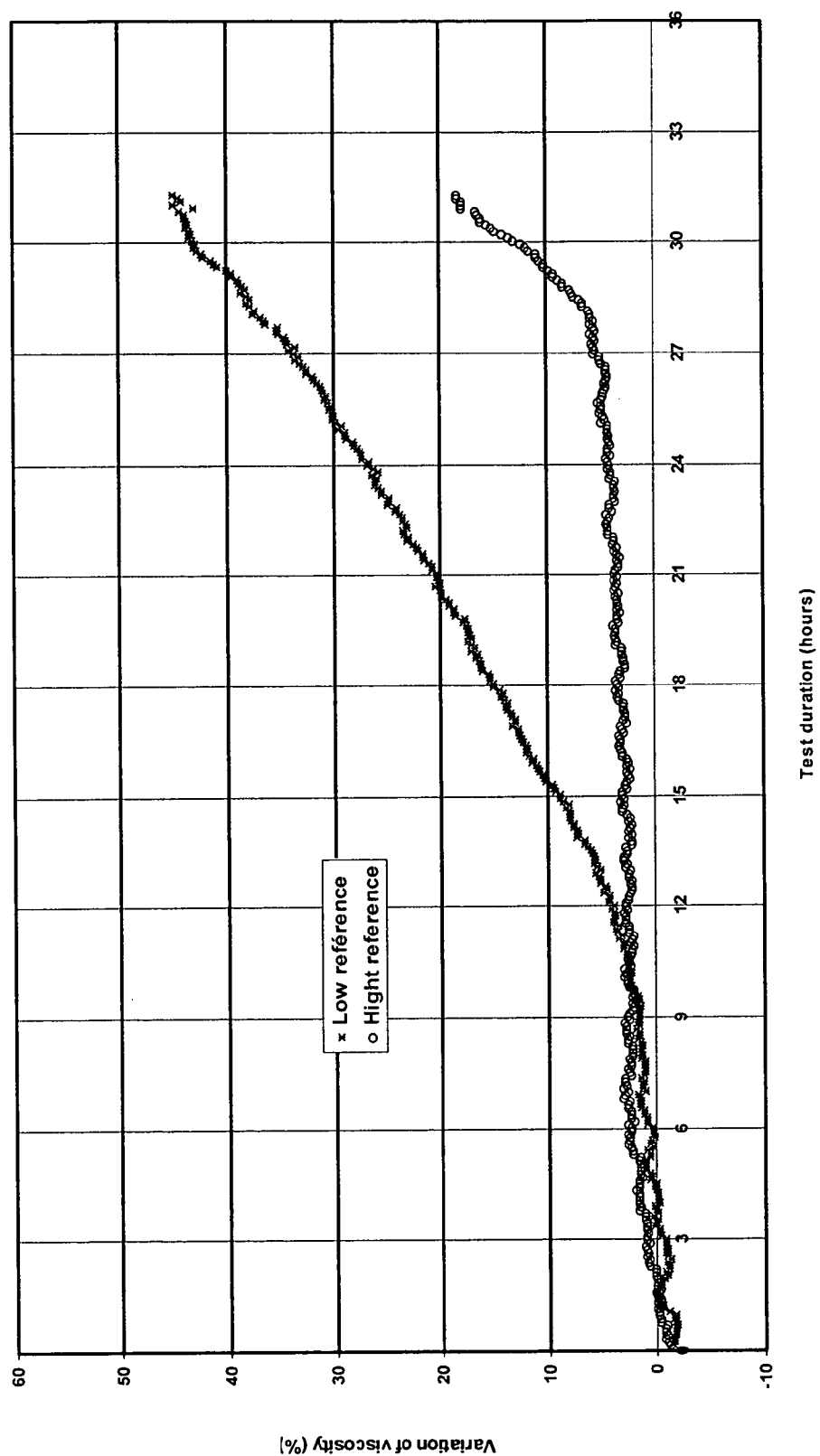
FIG. 8 is a nitro oxidation plot of variation of viscosity vs time generated by the alternate pressure viscometer device using a natural gas engine oil base reference

FIG. 8 shows the kind of curve we can record. An advantage demonstrated by this plot and during the measurement cycle is the real time observation of the behavior of products during oxidation tests.

Example 5

This example depicts an oxidation test. Here we investigated the behavior of a Viscosity Index Improver (VII) at 180° C. in a binary blend with a base oil. The VII selected in this test is a hydrogenated styrene isoprene and a petroleum Group 3 base oil. We include in this base oil the necessary quantity of VII to obtain a viscosity of 14 cSt at 100° C. By using two of the eight capillary devices described in Example 3, we record the viscosity of the base oil alone in the first cell and the blend of base oil and VII in the second cell. The test is done at a temperature of 180° C. TABLE 7 gives details of parameters for this example.

TABLE 7

| Example 5 parameters | |
|---|---|
| Oil quantity | 3 ml |
| Catalyst | No |
| Gas | Air |
| Gas pressure | 0.5 b |
| Gas flow | 1 l/h |
| Temperature | 180 ° C. |
| Reduced pressure | −110 mb |
| Internal diameter of the needle | 25 G |
| Length of the needle | 1" |
| Time to apply vacuum | 0.3 s |
| Measure duration | 5 s |
| Time between two serial of eight measures | 5 mn |

Figure 9:
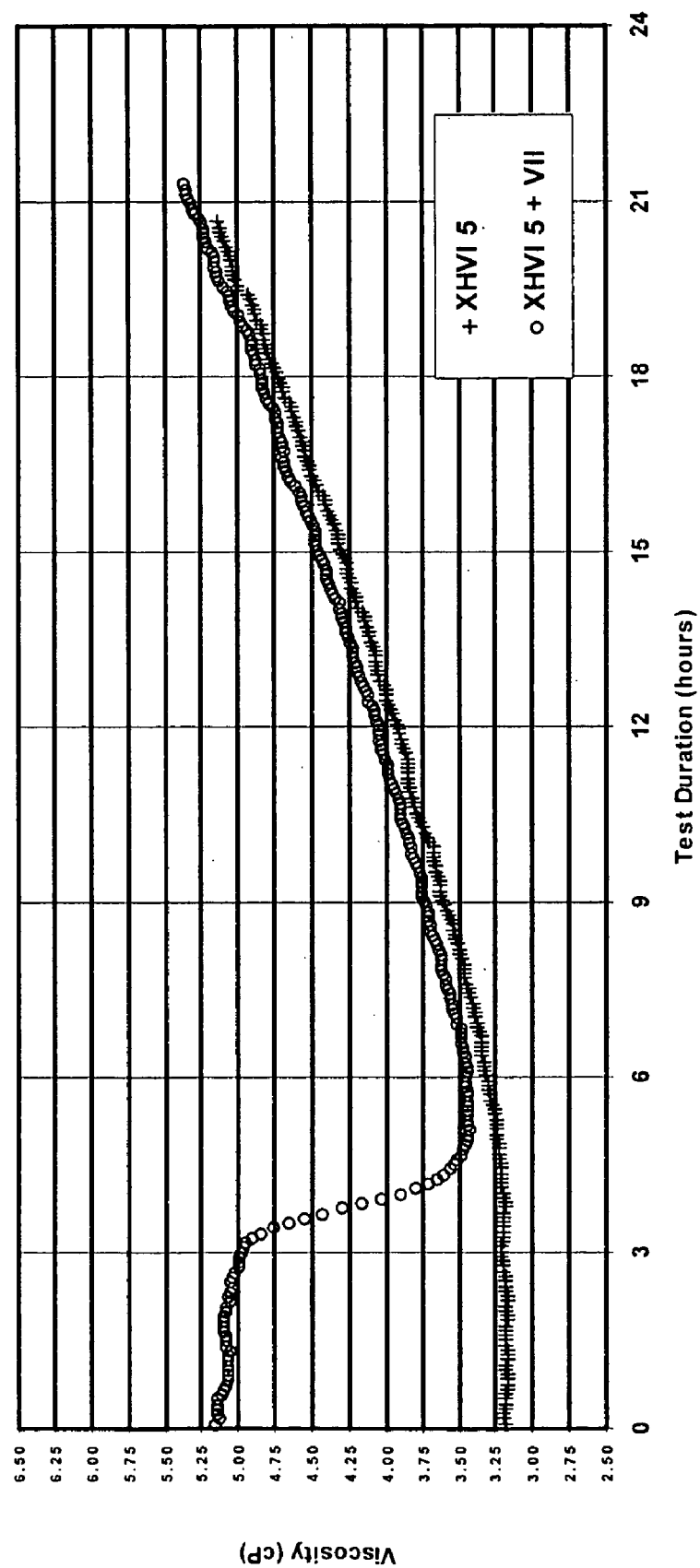
FIG. 9 is an oxidation test depicting the behavior of a Viscosity Index Improver (VII) in a binary blend with a base oil measuring the variation of viscosity vs time generated by the alternate pressure viscometer device

FIG. 9 shows a very rapid drop of the viscosity after around three hours of test which approaches the viscosity of the base oil after about 6 hours.

Example 6

Recording the variation of the viscosity versus time can show other performance attributes than oxidation. In this example we study the behavior of a dispersant additive. The role of a dispersant additive in engine oil is to maintain in suspension the carbon and other small particles which can appear in the oil. This additive protects the engine against plugging.

In the same procedure illustrated in Example 3 but at a temperature of 110° C. and using nitrogen (1 liter per hour) to prevent against any oxidation effect, we compared the viscosity variation of petroleum base oil, TOTAL 330Neutral (Group 1), where 2% of carbon black is well mixed before the test to the same oil where 2% of dispersant additive coming from the alkyl succinimide family is added. The introduction of carbon black in the oil increases the viscosity. If the carbon black remains in suspension in the oil, the viscosity remains at the same level. When the carbon black settles from suspension, the viscosity will decrease.

TABLE 8 gives details of parameters for this example. A difference between the procedures described above is the quantity of oil (5 ml versus 3 ml). The larger sample is due in part because the extremity of the capillary where $N_2$ is bubbled should be positioned approximately in the middle of the height of the oil in the reservoir and not at the bottom where carbon black decants. This positioning is to prevent against plugging the needle during a sample sequence.

TABLE 8

| Example 6 parameters | |
|---|---|
| Oil quantity | 5 ml |
| Catalyst | no |
| Gas | N2 |
| Gas pressure | 0.5 b |
| Gas flow | 1 l/h |
| Temperature | 110° C. |
| Reduced pressure | −110 mb |
| Internal diameter of the needle | 25 G |
| Length of the needle | 1" |
| Time to apply vacuum | 0.3 s |
| Measure duration | 5 s |
| Time between two serial of eight measures | 5 mn |

Figure 10:
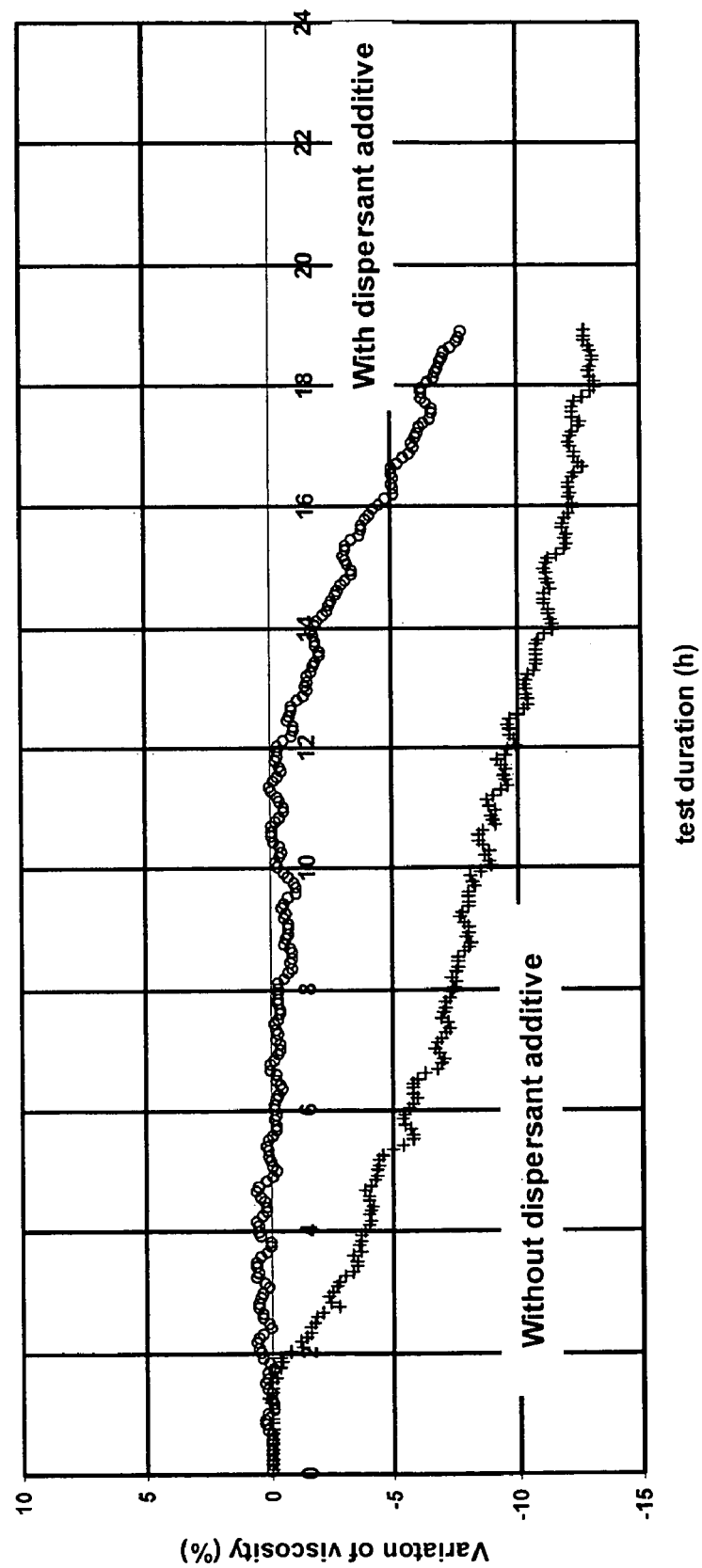
FIG. 10 is a dispersivity study plot measuring the variation of viscosity vs time generated by the alternate pressure viscometer device

FIG. 10 shows the rapid decrease of the viscosity of the oil which does not contain the dispersant. For the blend which contains the dispersant, the viscosity is constant for a long period of time with a decrease appearing after 12 hours.

What is claimed is:

1. A method for screening or determining a variation in viscosity of a fluid, the method comprising:
   a) providing a fluid sample to a reservoir placed in a thermostatic control system;
   b) placing a capillary in fluid communication with the fluid sample, wherein the capillary has a first end and a second end with a substantially uniform diameter over a predetermined length, the first end being submerged in the fluid sample to be measured, the second end attached to a manifold having at least one selectable valve, the capillary together with the manifold and the at least one selectable valve define a chamber of predetermined volume;
   c) actuating at least one selectable valve attached to the manifold to allow an oxidative gas to enter into and pass through the manifold and capillary;
   d) inducing the sample into the capillary by rapidly generating a dynamic differential pressure in the chamber thus allowing the sample to flow from the reservoir through the capillary;
   e) detecting pressure change of the chamber as a result of the fluid flow; and
   f) relating the rate of pressure change to the variation in viscosity.

2. The method of claim 1, wherein the viscosity is calculated from the Hagen-Poiseulle relation according to equation 2:

$$\mu = \frac{\pi R^4 \Delta P t}{8LV} \qquad (2)$$

wherein $\mu$ is the apparent viscosity, R is the radius of the capillary, L is the length of the capillary, t is time measured of the interval, $\Delta P$ is the pressure measurement over the interval and V is volume measured over the interval.

3. The method of claim 1, wherein the viscosity is calculated from a stored correlation of the pressure variation speed using at least two calibration fluids having known viscosities.

4. The method of claim 3, wherein the fluid sample is a non-Newtonian fluid.

5. The method of claim 1, wherein steps c-f are sequentially repeated under control of a computer.

6. The method of claim 1, wherein the thermostatic control system is maintained at a temperature between about 100° C. and about 200° C.

7. The method of claim 5, further comprising determining an oxidative breakdown parameter.

8. A method for measuring a relative increase in viscosity in a plurality of fluid samples comprising:
   a) providing a plurality of fluid samples into individual reservoirs, wherein the reservoirs are placed under thermostatic control;
   b) providing a plurality of capillary systems which provide a flow path for the fluid sample in a reservoir, each system having a capillary tube having a first end and a second end with a substantially uniform diameter over a predetermined length, the first end positionable and submerged in the fluid sample, the second end attached to a manifold having at least one selectable valve thereby defining a chamber of predetermined volume, the manifold having a pressure sensor;
   c) actuating at least one selectable valve attached to the manifold on each capillary system to allow an oxidation gas to enter into and pass through the manifold and capillary;
   d) switching the actuation in step c) and suddenly inducing the sample into the capillary by rapidly generating a dynamic differential pressure in the chamber thus allowing the sample to flow from the reservoir through the capillary;
   e) detecting pressure change of the chamber as a result of the fluid flow; and
   f) relating the rate of pressure change to an apparent viscosity property.

9. The method of claim 8, wherein the dynamic pressure differential is decreasing with fluid flow.

10. The method of claim 9, wherein steps c-f are sequentially repeated under control of a computer.

* * * * *